United States Patent [19]

Pappas et al.

[11] 3,947,459

[45] Mar. 30, 1976

[54] AQUEOUS PREPARATION OF SULFENAMIDES

[75] Inventors: Penelope R. Pappas, Akron; Dane K. Parker, Canton, both of Ohio

[73] Assignee: The Goodyear Tire & Rubber Company, Akron, Ohio

[22] Filed: Oct. 4, 1974

[21] Appl. No.: 512,807

[52] U.S. Cl. 260/293.57; 260/302 SN; 260/306.6 A
[51] Int. Cl.² ........................................ C07D 417/12
[58] Field of Search ................................ 260/293.57

[56] References Cited
UNITED STATES PATENTS

| | | |
|---|---|---|
| 2,045,888 | 6/1936 | Tschunkur et al. .................. 260/43 |
| 3,144,652 | 8/1964 | D'Amico .......................... 260/247.1 |
| 3,178,428 | 4/1965 | Eaker et al. ...................... 260/247.1 |

*Primary Examiner*—G. Thomas Todd
*Attorney, Agent, or Firm*—F. W. Brunner; J. M. Wallace, Jr.

[57] ABSTRACT

This invention relates to an improved process for preparing thiazolesulfenamides from aqueous chloramines and alkali metal salts of mercaptothiazoles, in water. The chloramine mixture can be prepared from amines or aqueous amine salt solutions.

23 Claims, No Drawings

AQUEOUS PREPARATION OF SULFENAMIDES

The present invention relates to thiazolesulfenamides and to an improved process for their preparation in water.

These sulfenamides are known to be good accelerators in the vulcanization of natural and synthetic rubbers. These materials do not exhibit early vulcanization, known in the art as scorch, and complete vulcanization quickly once the vulcanization temperature has been reached.

Aqueous preparation of these sulfenamides from sodium mercaptobenzothiazole solutions have been reported. Canadian Pat. No. 890,433 discusses the preparation of 2-(3-methylpiperidinothio)-benzothiazole using bleach oxidation of an aqueous mixture of 3-methylpiperidine and sodium mercaptobenzothiazole. This process was carried out in water and various organic solvents, and required temperatures of 70° C., reaction times of about 3 hours and purification of the product by extraction and distillation. Preparations using other amines such as t-butylamine often require addition of a mineral acid to maintain a satisfactory pH during reaction.

Sulfenamide preparations from chloramines are also well known in the art. Generally the chloramine is first formed in an aqueous medium and isolated before use in sulfenamide preparation.

It is an object of the present invention to provide an improved process for the aqueous preparation of sulfenamides from alkali metal salts of mercaptothiazoles and amine or amine salt starting materials. Other objects will become apparent to those skilled in this art as the description proceeds.

It has been discovered in accordance with the present invention that certain thiazolesulfenamides can be prepared in aqueous media in high yields by utilizing a novel method of combining the reactants. Isolation of the chloramine or addition of acid is not necessary. The reaction is rapid and extensive product purification is unnecessary. The process comprises 1. combining an amine and aqueous NaOCl at about 0° C. to 25° C. forming an aqueous chloramine mixture,
2. adding a concentrated aqueous solution of an alkali metal salt of a mercaptothiazole to the chloramine mixture,
3. allowing the resulting exotherm to reach about 25° to 50° C.,
4. agitating the mixture for from 5 to 30 minutes,
5. cooling the mixture to 25° C. or less, wherein the product solidifies, before,
6. separating and water-washing the product.

The reaction is carried out in water. Maximum reaction time to obtain the final product is around one hour, contrasted with the three or more hours of the prior art. The reaction is exothermic compared to the prior art requirement of heating to a temperature of 70° C. or more. The product requires no purification; simple filtration and water washing yields the final product in contrast to the prior art processes which often require extraction and distillation. An aqueous mixture of chloramine can be used in place of the purified chloramine taught to be necessary in the prior art.

The amine source can be either pure amine or an amine salt solution. When amine salt solutions are used, they can be neutralized in situ during the chloramine formation, using the base generated from the reduction of the hypochlorite. Supplementation of an additional equivalent of base has been found to be necessary to maintain a satisfactory pH during the sulfenamide formation. Use of amine salt solutions is of particular advantage in the cases of sulfenamides derived from alkylpiperidines. A convenient source of alkylpiperidines is the reduction of alkylpyridinium salts in aqueous media, to the corresponding alkylpiperidinium salts, which can be used directly to produce sulfenamide accelerators. No isolation or purification of the amine is necessary.

The amine salt solutions can be preneutralized before use in the sulfenamide preparation yielding a crude aqueous amine. The crude aqueous amine derived from the preneutralization can be used in the process without further purification.

Representative examples of amines useful in the practice of the present invention are t-butylamine, isopropylamine, cyclohexylamine, hexamethyleneimine and alkyl substituted piperidines and pyrrolidines substituted in the 3 and 4 positions wherein the alkyl groups contain from 1 to 4 carbon atoms. Representative examples of such substituted piperidines and pyrrolidines are 3-n-butylpiperidine, 3-methylpiperidine, 4-methylpiperidine and 3-methylpyrrolidine.

Representative examples of sulfenamide products produced using the process of the present invention are 2-(3-methylpiperidinothio)-benzothiazole, 2-(4-methylpiperidinothio)-benzothiazole, 2-t-butylaminothiobenzothiazole, 2-isopropylaminothiobenzothiazole, 2-cyclohexylaminothiobenzothiazole and 2-hexamethyleneiminothiobenzothiazole.

Representative examples of alkali metal salts of mercaptothiazoles useful in the practice of the present invention are the alkali metal salts of 2-mercaptothiazole,
2-mercapto-4-methylthiazole,
4-ethyl-2-mercaptothiazole,
2-mercapto-4-n-propylthiazole,
4-n-butyl-2-mercaptothiazole,
2-mercapto-4,5-dimethylthiazole,
4,5-diethyl-2-mercaptothiazole,
2-mercapto-4,5-n-propylthiazole,
4,5-di-n-butyl-2-mercaptothiazole,
2-mercapto-4-phenylthiazole,
2-mercaptobenzothiazole,
2-mercapto-4-phenylbenzothiazole,
2-mercapto-6-phenylbenzothiazole,
2-mercaptotetrahydrobenzothiazole,
2-mercaptonaphthothiazole,
4-chloro-2-mercaptobenzothiazole,
5-acetyl-2-mercapto-4-methylthiazole, and
5-carbethoxy-2-mercapto-4-methylthiazole.

Representative examples of useful alkali metals are sodium and potassium.

Preferred sulfenamide products are those having a melting point at or above 40° C., such as 2-(3-methylpiperidinothio)-benzothiazole, 2-(4-methylpiperidinothio)-benzothiazole, 2-t-butylaminothiobenzothiazole, 2-cyclohexylaminothiabenzothiazole, 2-hexamethyleneiminothiobenzothiazole, 5-carbethoxy-4-methyl-2-(3-methylpiperidinothio)-thiazole.

Preferred amounts of reactants are from 15 to 25 percent excess of amine, and from 15 to 25 percent excess of bleach, based on the weight of the benzothiazole. Excess of amine or bleach is not necessary, although decreased yields may be realized at low excesses.

Preferred temperature range for the sulfenamide formation is from 20° to 60° C., but from 25° to 40° C. is most preferred. The preferred temperature range for chloramine formation is from 0° to 25° C. The concentration of the aqueous alkali mercaptothiazole should be at least 20 weight percent theoretical mercaptothiazole.

Preferred concentrations of the aqueous solution of alkali metal salt of a mercaptothiazole range from 30 to 50 weight percent theoretical mercaptothiazole.

Preferred bases for the in situ neutralization of amine salts are sodium hydroxide, potassium hydroxide, and sodium carbonate.

The invention is more concretely described with reference to the examples below, wherein all parts and percentages are by weight unless otherwise indicated. Example 1 shows the preparation of 2-(3-methylpiperidinothio)-benzothiazole from 3-methylpiperidine and sodium mercaptobenzothiazole. Example 2 illustrates the preparation of 2-(4-methylpiperidinothio)-benzothiazole from 4-methylpiperidinium sulfate. Example 3 illustrates the preparation of 2-t-butylaminothiobenzothiazole.

EXAMPLE 1

A 250 milliliter, three-neck, round bottom flask was fitted with a mechanical stirrer, thermometer, addition funnel and an outlet to the atmosphere. The flask was charged with 99.3 milliliters (0.24 m) cold bleach (2.42 M, 9.36 grams NaOH/liter). The amine, 3-methylpiperidine, (23.78 grams, 0.24 m), was added dropwise while cooling the flask to keep the temperature below 25° C. Two liquid phases result, the upper phase being the chloramine. Sodium mercaptobenzothiazole solution (70.74 grams, 47.3% theoretical mercaptobenzothiazole) was added to the chloramine mixture dropwise over a two minute period. The temperature ranged from 25° to 38° C. without external temperature control while a milky-white emulsion formed. The emulsion was stirred at 48° to 31° C. for 25 minutes during which time the product solidified. The mixture was cooled to 22° C. and filtered. The filter cake was thoroughly water washed and dried at 40° C. The product was obtained as an off-white granular material in 98.2% theoretical yield with a melting point of 59.5° to 62° C. The purity was rated at 97.2% by reduction of the sulfenamide followed by titration of the liberated amine.

EXAMPLE 2

A flask equipped as described in Example 1 was charged with 25.6 milliliters bleach (0.065 m, 2.39 M, 9.49 grams NaOH/liter) and cooled to maintain the temperature below 25° C. Dropwise addition of 18.5 grams (0.06 m) of 4-methylpiperidinium sulfate solution, (32.1% theoretical amine content) was made, followed by the addition of 2.4 grams (0.06 m) of NaOH in 10 milliliters of water. Addition of 17.6 grams (0.05 m) of a solution of sodium mercaptobenzothiazole (47.3% theoretical mercaptobenzothiazole) was added dropwise over 5 minutes, allowing the temperature to range from 15° to 36° C. The mixture was stirred for 15 minutes at 30° to 36° C. The mixture was cooled to 10° C., whereupon the product solidified and was separated from solution. The off-white, solid product was washed thoroughly with water and dried at 40° C. The yield was 87.5% of 2-(4-methylpiperidinothio)-benzothiazole with a melting point of 46° to 49.5° C. The purity was rated at 98.7% using the reduction-titration method described in Example 1.

EXAMPLE 3

A 500 milliliter flask equipped as described above was charged with 105.2 milliliters bleach (0.24 m, 2.28 M, 9.33 grams NaOH/liter). The bleach was cooled in an ice water bath while 17.52 grams (0.24 m) of t-butylamine was added dropwise at 10° to 15° C., followed by 70.6 grams (0.20 m) sodium mercaptobenzothiazole solution, (47.3% theoretical mercaptobenzothiazole) added dropwise at 15° C. to 23° C. over a 15 to 20 minute period. A milky-white emulsion formed. The product solidified after stirring the emulsion for 25 minutes. The mixture was suction filtered. The filter cake was water washed and dried at 40° C. The off-white powdery product was 2-t-butylaminothiobenzothiazole, 89.5 percent of theoretical yield, having a melting point of 103° to 105° C.

Examples 4 through 7 were carried out in the same manner and using the same mole ratios described in Example 3. The various amines tested and the results obtained are shown in Table I.

Table I

| Ex. | Amine | Sulfenamide | Yield (%) | Melting Point (°C.) | Purity |
|---|---|---|---|---|---|
| 4 | t-butylamine | 2-t-butylaminothio-benzothiazole | 85.0 | 100–104 | 95.6 |
| 5 | isopropylamine | 2-isopropylamino-thiobenzothiazole | 70.6 | 87–91 | — |
| 6 | cyclohexylamine | 2-cyclohexylamino-thiobenzothiazole | 93.8 | 90–95 | 92.8 |
| 7 | hexamethyleneimine | 2-hexamethyleneimino-thiobenzothiazole | 98.4 | 89–94 | 92.7 |

The sulfenamides can be readily prepared via neutralization of the amine salt in situ as shown in Example 2, but preneutralization is also possible and provides the advantage of lessening the total reaction solution volume. When using preneutralization, the crude amine is used as shown in the method of Example 1.

While certain representative embodiments and details have been shown for the purpose of illustrating the invention, it will be apparent to those skilled in this art that various changes and modifications may be made therein without departing from the spirit or scope of the invention.

We claim:

1. An improved process for the preparation of sulfenamides by combining an aqueous solution of an alkali metal salt of a mercaptothiazole with an amine and bleach and reacting the mixture, the improvement comprising a. adding an amine to bleach to form a chloramine mixture,
b. adding the aqueous solution of an alkali metal salt of a mercaptothiazole to the chloramine mixture,
c. allowing the reaction to take place, and
d. separating and water-washing the sulfenamide.

2. A process as described in claim 1 wherein the amine and bleach are in a 15 to 25 percent excess based on the mercaptothiazole.

3. A process as described in claim 1 wherein the aqueous solution of an alkali metal salt of a mercaptothiazole is in a concentration of from 30 to 50 weight percent of theoretical mercaptothiazole.

4. A process as described in claim 1 wherein the mercaptothiazole is mercaptobenzothiazole.

5. A process as described in claim 3 wherein the chloramine is cooled to a temperature at or below 25° C. before the aqueous solution of alkali metal salt of mercaptothiazole is added.

6. A process as described in claim 3 wherein the sulfenamide product is dried at 40° C. after water washing.

7. A process as described in claim 3 wherein the amine is t-butylamine, 3-methylpiperidine and 4-methylpiperidine, and the thiazole is mercaptobenzothiazole.

8. A process as described in claim 3 wherein the amine is cyclohexylamine.

9. A process as described in claim 3 wherein the amine is hexamethyleneimine.

10. A process as described in claim 3 wherein the amine is 3-methylpiperidine.

11. A process as described in claim 3 wherein the amine is 4-methylpiperidine.

12. A process as described in claim 3 wherein the amine is selected from the group consisting of isopropylamine, 3-methylpyrrolidine, and 3-n-butylpyrrolidine.

13. A process as described in claim 1 wherein the alkali metal salt of a mercaptothiazole is selected from the group consisting of the sodium or potassium salt of
2-mercaptothiazole,
2-mercapto-4-methylthiazole,
4-ethyl-2-mercaptothiazole,
2-mercapto-4-n-propylthiazole,
4-n-butyl-2-mercaptothiazole,
2-mercapto-4,5-dimethylthiazole,
4,5-diethyl-2-mercaptothiazole,
2-mercapto-4,5-di-n-propylthiazole,
4,5-di-n-butyl-2-mercaptothiazole,
2-mercapto-4-phenylthiazole,
2-mercaptobenzothiazole,
2-mercapto-4-phenylbenzothiazole,
2-mercapto-6-phenylbenzothiazole,
2-mercaptotetrahydrobenzothiazole,
2-mercaptonaphthothiazole,
4-chloro-2-mercaptobenzothiazole,
5-acetyl-2-mercapto-4-methylthiazole, and
5-carbethoxy-2-mercapto-4-methylthiazole.

14. A process for the preparation of sulfenamides comprising
a. adding an amine salt solution to bleach to form a chloramine mixture,
b. adding a base to the chloramine mixture,
c. adding an aqueous alkali sodium or potassium mercaptobenzothiazole to the chloramine mixture,
d. allowing the reaction to take place, and
e. separating and water washing the sulfenamide.

15. A process as described in claim 14 wherein the amine salt and bleach are in a 15 to 25 percent excess based on the mercaptothiazole.

16. A process as described in claim 14 wherein the aqueous solution of an alkali metal salt of a mercaptothiazole is in a concentration of from 30 to 50 weight percent theoretical mercaptothiazole.

17. A process as described in claim 14 wherein the mercaptothiazole is selected from the group consisting of alkali metal salts of
2-mercaptothiazole,
2-mercapto-4-methylthiazole,
4-ethyl-2-mercaptothiazole,
2-mercapto-4-n-propylthiazole,
4-n-butyl-2-mercaptothiazole,
2-mercapto-4,5-dimethylthiazole,
4,5-diethyl-2-mercaptothiazole,
2-mercapto-4,5-di-n-propylthiazole,
4,5-di-n-butyl-2-mercaptothiazole,
2-mercapto-4-phenylthiazole,
2-mercaptobenzothiazole,
2-mercapto-4-phenylbenzothiazole,
2-mercapto-6-phenylbenzothiazole,
2-mercaptotetrahydrobenzothiazole,
2-mercaptonaphthothiazole,
4-chloro-2-mercaptobenzothiazole,
5-acetyl-2-mercapto-4-methylthiazole, and
5-carbethoxy-2-mercapto-4-methylthiazole.

18. A process as described in claim 14 wherein the mercaptothiazole is mercaptobenzothiazole.

19. A process as described in claim 18 wherein the chloramine is cooled to a temperature at or below 25° C. before the aqueous alkali mercaptothiazole is added.

20. A process as described in claim 18 wherein the sulfenamide product is dried at 40° C. after water washing.

21. A process as described in claim 18 wherein the amine salt is selected from the group consisting of 3-methylpiperidinium sulfate, 3-methylpiperidinium acetate, 3-methylpiperidinium chloride and 3-methylpiperidinium phosphate.

22. A process as described in claim 18 wherein the amine salt is selected from the group consisting of 4-methylpiperidinium sulfate, 3-methylpiperidinium acetate, 4-methylpiperidinium chloride, and 4-methylpiperidinium phosphate.

23. A process as described in claim 14 wherein the base is selected from the group consisting of sodium hydroxide, potassium hydroxide and sodium carbonate.

* * * * *

Disclaimer 3,947,459.—*Penelope R. Pappas*, Akron and *Dane K. Parker*, Canton, Ohio. AQUEOUS PREPARATION OF SULFENAMIDES. Patent dated Mar. 30, 1976. Disclaimer filed Oct. 28, 1981, by the assignee, *The Goodyear Tire & Rubber Co.*

Hereby enters this disclaimer to claims 1 through 13 of said patent.

[*Official Gazette Jan. 5, 1982*]